(12) United States Patent
Lee

(10) Patent No.: US 8,111,899 B2
(45) Date of Patent: Feb. 7, 2012

(54) SUBSTRATE-CHECK EQUIPMENT

(76) Inventor: Hui-Hsiung Lee, Taipei (TW)

( * ) Notice: Subject to any disclaimer, the term of this patent is extended or adjusted under 35 U.S.C. 154(b) by 852 days.

(21) Appl. No.: 12/218,005

(22) Filed: Jul. 10, 2008

(65) Prior Publication Data
US 2010/0008560 A1 Jan. 14, 2010

(51) Int. Cl.
G01N 21/00 (2006.01)
G06K 9/00 (2006.01)
(52) U.S. Cl. .................. 382/141; 356/237.1; 356/237.2
(58) Field of Classification Search .................. 382/141, 382/149, 100, 103, 151, 112; 356/237.1, 356/237.2, 239, 7, 241.6, 429, 448
See application file for complete search history.

(56) References Cited

U.S. PATENT DOCUMENTS

| 5,963,328 | A  | * | 10/1999 | Yoshida et al. | ............... | 356/600 |
| 6,954,268 | B2 | * | 10/2005 | Naiki et al. | ................ | 356/237.2 |
| 7,899,238 | B2 | * | 3/2011 | Tabata | .......................... | 382/141 |
| 2007/0206183 | A1 | * | 9/2007 | Lebens | ....................... | 356/237.2 |

* cited by examiner

Primary Examiner — Layla Lauchman

(57) ABSTRACT

A substrate-check equipment has a conveyer, at least two lamps, at least two image acquisition units and a control unit. The conveyer conveys a substrate. The lamps are mounted respectively above and below the conveyer to respectively shine light onto the substrate. Each lamp has an adjusting unit for adjusting intensity of the lamp. The image acquisition units correspond to the lamps and are mounted respectively above and below the conveyer to respectively capture images of the substrate and generate image signals. The control unit is electronically connected to the lamp and the image acquisition units. Emitted light intensity of the lamps is adjusted to ensure consistent image quality and speed up procedures for checking the substrate.

8 Claims, 4 Drawing Sheets

SUBSTRATE-CHECK EQUIPMENT

BACKGROUND OF THE INVENTION

1. Field of Invention

The present invention relates to a substrate-check equipment, and more particularly to a substrate-check equipment that changes light intensity of a lamp to maintain captured image quality and quickly check a substrate.

2. Description of the Related Art

A substrate such as paper, glass, a fabric covered with a layer of resin or multiple layers of fibers formed on a substrate such as paper, glass, a fabric covered by impregnation methods is required to have excellent consistency of parameters for a high-value product.

Generally, a quality of the substrate can be determined by checking upper and lower surfaces of the substrate. A traditional method for checking the upper and the lower surfaces comprises turning over the substrate by operational personnel after checking one of the surfaces, but this wastes timetherefore robotic substrate-check equipment were used to turn over the substrate conveniently.

A conventional automatic substrate-check equipment comprises at least one conveyer, at least two image acquisition units, at least two lamps and a control unit. The conveyer is pervious to light. The lamp corresponds respectively to the image acquisition units. The control unit connects electrically to and controls the conveyer, the image acquisition units and the lamp. The control unit allows the conveyer to convey a substrate and allows the lamps to respectively face and emit lights to the upper and lower surfaces of the substrate. The upper and lower surfaces respectively reflect the lights. The image acquisition units respectively capture reflected light from the upper and lower surfaces to generate signals that are received by the control unit. After analyzing the signals by the control unit, the quality of the substrate can be determined.

However, substrates can be made of various materials and have various thicknesses. Furthermore, a substrate is designed to have thin portions and thick portions. The image acquisition unit of the conventional substrate-check equipment is a camera with a linear charge coupled device (linear CCD). The lamp of the conventional substrate-check equipment has a light source with a constant intensity. Consequently, reflected light reflected by the thick parts of the substrate is dark, which may not be captured clearly by the camera with the CCD and would lead to an inaccurate reading of the quality of the substrate.

The inaccurate reading can be eliminated by adjusting an aperture of a camera lens. When shooting the thick parts of the substrate, the aperture has to be enlarged. When shooting thin parts of the substrate, the aperture has to be narrowed. However, the aperture is adjusted by operational personnel, and consumes much time, conditions of the control unit for analyzing signals are also required to be adjusted and calibrated. Therefore, adjustments make a quality check procedure complicated and inconvenient.

To overcome the shortcomings, the present invention provides a substrate-check equipment to mitigate or obviate the aforementioned.

SUMMARY OF THE INVENTION

The primary objective of the present invention is to provide a substrate-check equipment that changes light intensity of a lamp to ensure consistent captured image quality and quickly check a substrate.

To achieve the objective, the substrate-check equipment in accordance with the present invention has a conveyer, at least two lamps, at least two image acquisition units and a control unit. The conveyer conveys a substrate. The lamps are mounted respectively above and below the conveyer to respectively shine light onto the substrate. Each lamp has an adjusting unit for adjusting intensity of the lamp. The image acquisition units corresponds to the lamps and are mounted respectively above and below the conveyer to respectively capture images of the substrate and generate image signals. The control unit is electronically connected to the lamp and the image acquisition units. Emitted light intensity of lamps is adjusted to ensure consistent image quality and speed up procedures for checking the substrate.

Other objectives, advantages and novel features of the invention will become more apparent from the following detailed description when taken in conjunction with the accompanying drawings.

DETAILED DESCRIPTION OF THE INVENTION

Figure 1:
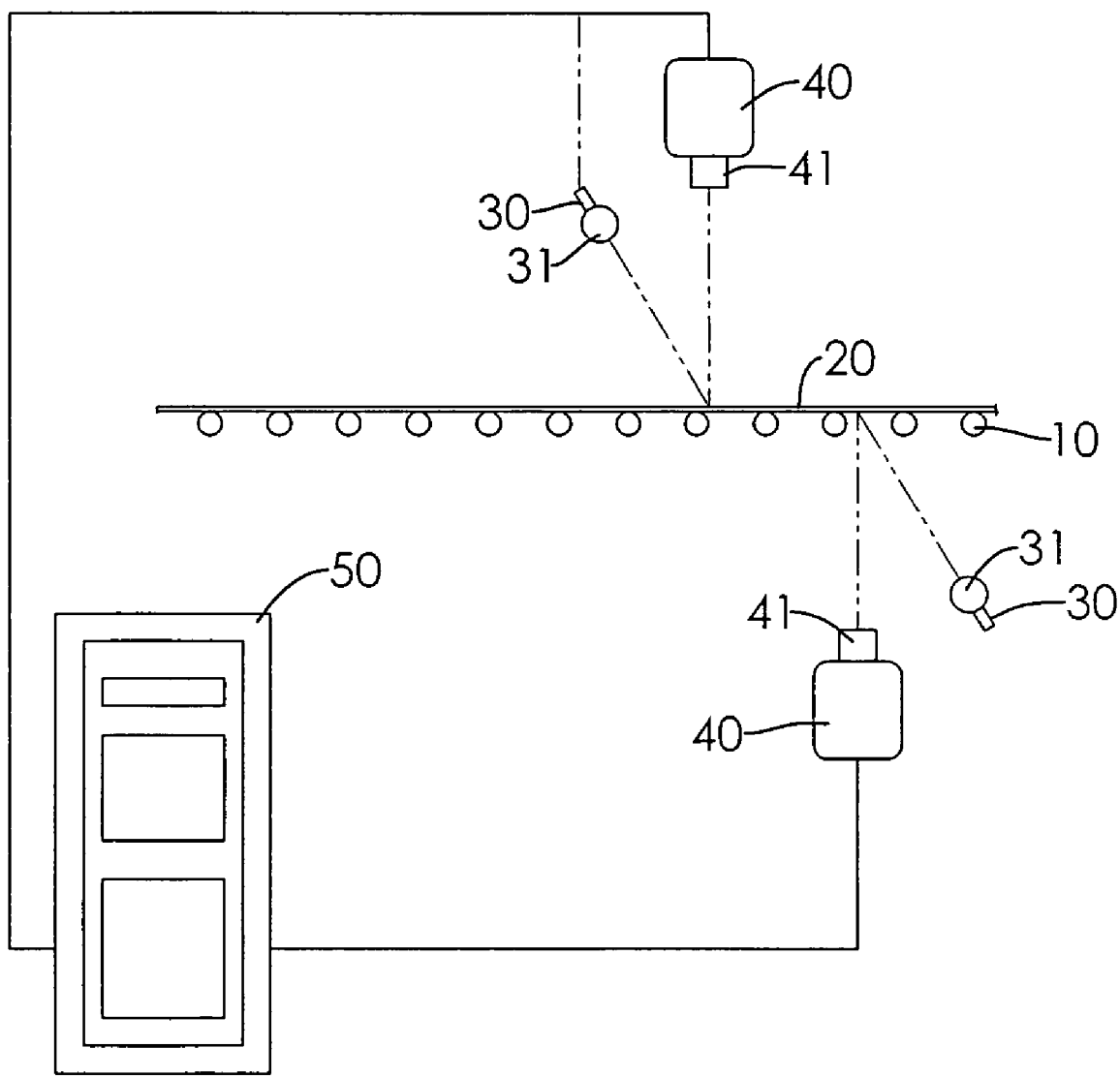
FIG. 1 is a schematic side view of substrate-check equipment in accordance with the present invention.
Figure 2:
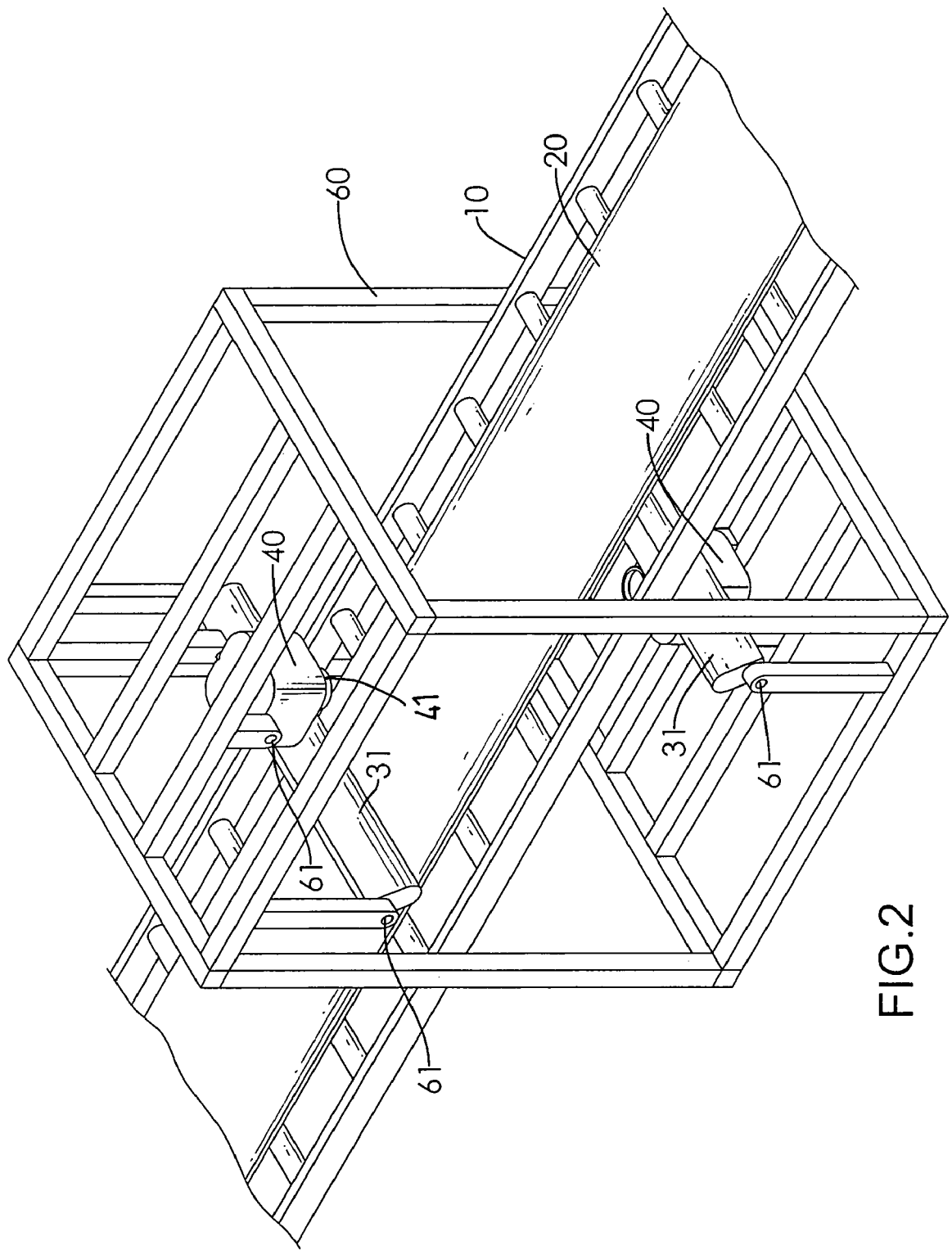
FIG. 2 is a perspective view of the substrate-check equipment in FIG. 1.
Figure 3:
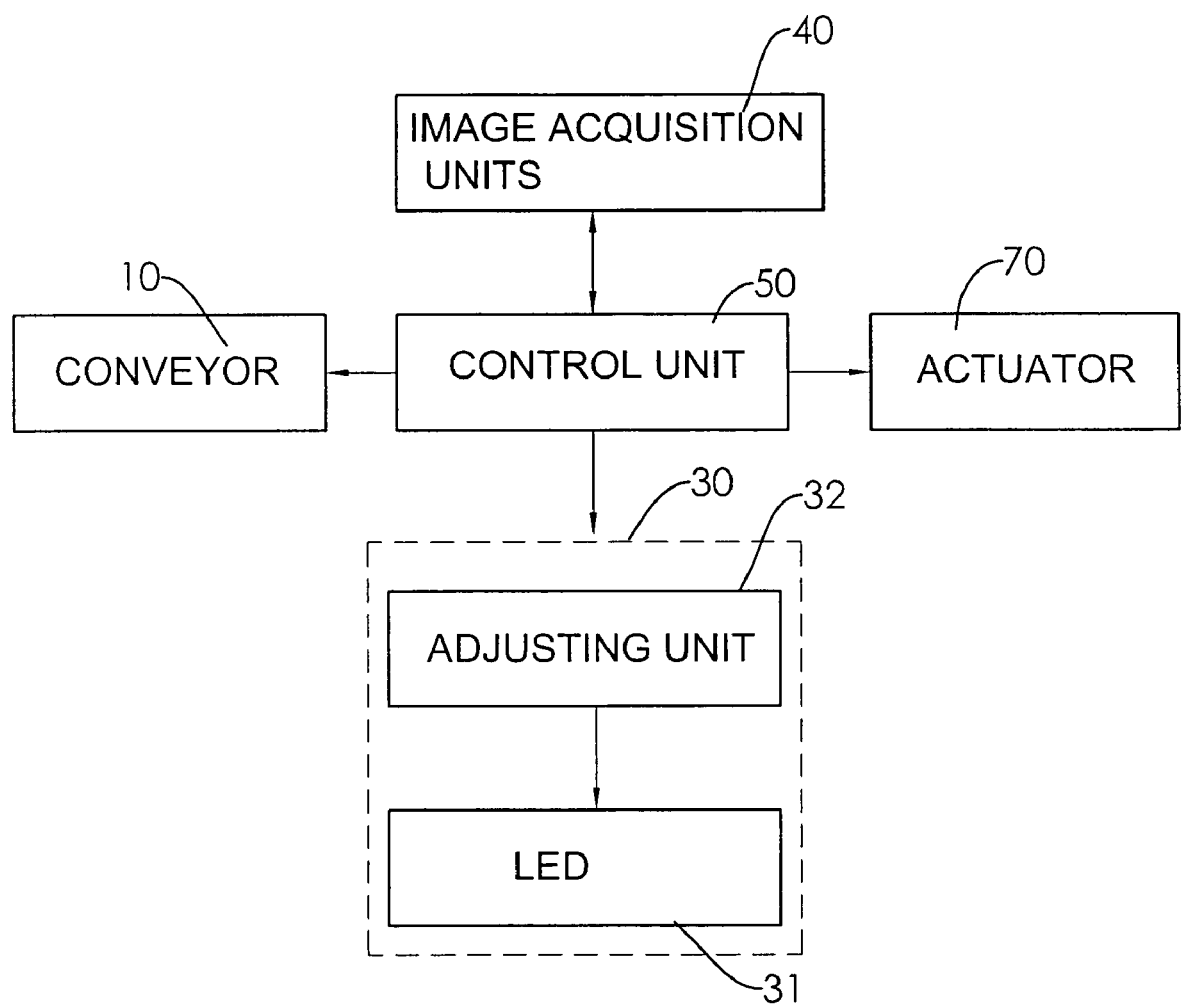
FIG. 3 is a block diagram of the substrate-check equipment in FIG. 1.

With reference to FIGS. 1 to 3, substrate-check equipment in accordance with the present invention has a frame (60), a conveyer (10), at least two lamps (30), at least two image acquisition units (40), at least two actuators (70) and a control unit (50).

The conveyer (10) conveys a substrate and may be pervious to light, mounted through the frame (60) and conveys substrates (20) through the frame (10). The conveyer (10) has an upper surface and a lower surface and may comprise multiple rollers and at least one drive roller, and may further comprise a pervious belt abutting the rollers and being driven to rotate by the at least one driven roller. The rollers are separately disposed along the conveyor perpendicular to a direction of travel and are separated by gaps.

The lamps (30) are mounted pivotally on the frame (60) using mounting brackets (61) and are mounted respectively above the upper surface of the conveyer (10) and below the lower surface of the conveyer (10) to respectively shine light onto the upper and lower surfaces of the conveyer (10) and may be disposed in the gaps between rollers. Each lamp (30) comprises a light emitted diode (LED) light (31) and an adjusting unit (32). A preferred LED light (31) is a LED tubular lights. The adjusting unit (32) is connected electrically to the LED light (31) to adjust an intensity of light emitted from the lamp (30), may be to adjust intensity of light emitted from the LED light (31) and may be mounted adjacent to the LED light (31) or be mounted in the LED light (31).LED tubular lights The image acquisition units (40) are mounted pivotally on the frame (60) using mounting brackets (61), correspond respectively to the lamps (30) and are mounted respectively above the upper surface of the conveyer (10) and below the lower surface of the conveyer (10) to respectively acquire images of the substrate from above and below the conveyor (10) and generate image signals and may be disposed in the gaps between rollers of the conveyor (10). Each image acquisition unit (40) may be a camera with a linear charge coupled device (linear CCD) to allow the camera to scan and linearly shoot the surface of the substrate (20) to obtain a linear image and generate an image signal. The camera has a lens (41) with a constant aperture size.

The actuators (70) are mounted on the frame (60), correspond to the lamps (30) and the image acquisition units (40) and are connected electronically to the mounting brackets (61) to control the LED light (31) and the camera to pivot relative to the substrate (20) to required angles.

The control unit (50) stores image processing software and is connected electronically to the lamp (30), the image acquisition units (40) and the actuators (70) and may further be connected electronically to the conveyer (10). The control unit (50) controls the lamps (30), may control the LED light (31) and controls the adjusting unit (32) of each lamp (30) to emit light of specific intensity according to a thickness of the substrate. The control unit (50) controls the image acquisition units (40) to receive linear image signals from the camera, which is analyzed by the image processing software and may be connected electronically to the sensors to receive the signal of the light intensity adjacent to the lens of the camera. The control unit (50) controls the actuators (70) to adjust the angles of the camera and the LED light (31) facing the substrate (20). The control unit (50) controls movement of the conveyer (10) conveying the substrate (20).

The linear image obtained by the camera with CCD is an image of a segment of the substrate (20), data capacity of the linear image is limited to ensure analysis by the image processing software of the control unit (50) corresponds to a speed of the conveyor (10). Therefore, the control unit (50) may change a size of the segment, number of pixel equivalents of the segment and speed of the conveyor according to a processor speed.

Figure 4:
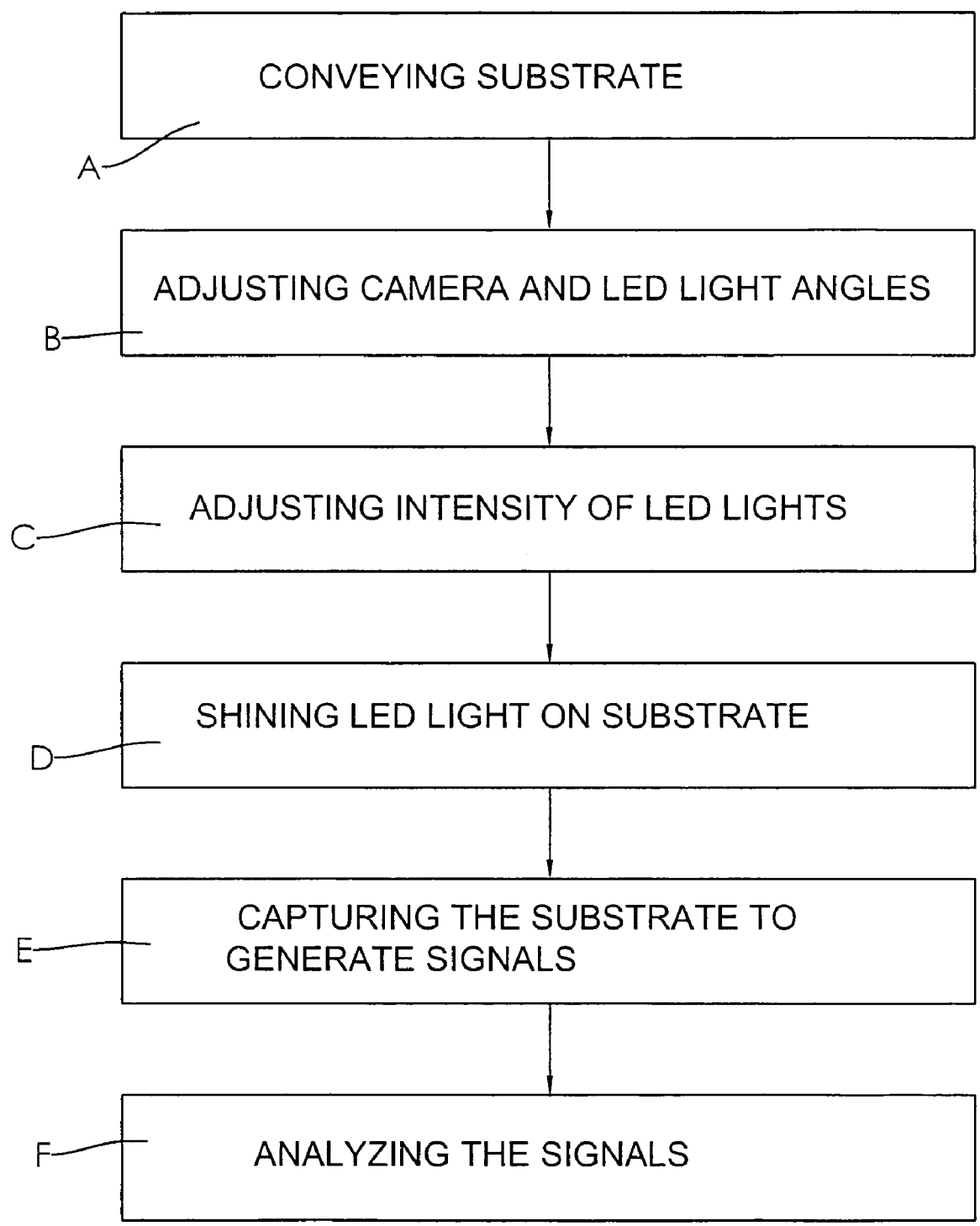
FIG. 4 is a flow diagram of a method of checking a substrate in accordance with the present invention.

With further reference to FIG. 4, a preferred method of checking a substrate (20) comprises acts of (A) conveying substrate, (B) adjusting camera and LED light (31) angles, (C) adjusting intensity of the LED lights (31), (D) shining LED lights (31) on the substrate (20), capturing the substrate (20) to generate signals and analyzing the signals with the control unit (50).

The act of (A) conveying the substrate (20) comprises the control unit (50) actuating the conveyor (10) having a substrate (20) mounted thereon to stop, start, move forward, backward and a speed of movement.

The act of (B) adjusting the camera and LED light (31) angles comprises the control unit (50) changing angles of the camera and the LED light (31) relative to the conveyor (10) and substrate (20).

The act of (C) adjusting intensity of LED light (31) comprises the control unit (50) actuating the adjusting unit (32) to alter an intensity of the LED lights (31) and ensure a light reading at the camera corresponds to operational parameters. The intensity may be altered by changing voltage of the LED lights (31), moving a filter having variable translucency over the LED lights (31), selectively turning the LED lights (31) on or off, changing a percentage of a reflective surface coincident with light emitted from the LED lights (31) and therefore shining on the substrate (20), altering a lens to change a dispersion and focus of the light emitted from the LED lights (31) or the like. The intensity is preferred altered by changing voltage of the LED lights (31).

The act of (E) capturing the substrate (20) to generate signals comprises the control unit (50) actuating the camera to record an image of the substrate, converting the image to signals and sending the signals to the control unit (50).

The act of (F) analyzing the signal comprises the control unit (50) actuating image processing software to analyze the signal.

When the substrate (20) is thick, intensity of the LED light (31) is increased. When the substrate (20) is thin, the intensity of the LED light (31) is decreased. The control unit (50) or operational personnel control the control unit (50) to adjust the intensity of the LED light (31) rather than adjust an aperture of a camera by hand. Therefore, the substrate-checking equipment of the present invention speed up the procedure for checking the substrate (20).

Even though numerous characteristics and advantages of the present invention have been set forth in the foregoing description, together with details of the structure and function of the invention, the disclosure is illustrative only. Changes may be made in detail, especially in matters of shape, size and arrangement of parts within the principles of the invention to the full extent indicated by the broad general meaning of the terms in which the appended claims are expressed.

What is claimed is:

1. A substrate-check equipment comprising:
a frame;
a conveyer mounted through the frame and having an upper surface and an lower surface and being adapted to convey a substrate;
at least two lamps mounted pivotally on the frame using mounting brackets and respectively above the upper surface of the conveyer and below the lower surface of the conveyer to respectively shine light onto the upper and lower surfaces of the conveyer and each of the at least two lamps having an adjusting unit for adjusting intensity of light emitted from the lamp;
at least two image acquisition units corresponding to the lamps and being mounted pivotally on the frame using mounting brackets and respectively above the upper surface of the conveyer and below the lower surface of the conveyer to respectively acquire images of a substrate and generating image signals;
a control unit being connected electronically to the lamps and the image acquisition units to control the adjusting unit of each lamp to emit light with a specific intensity and receiving image signals from the image acquisition units; and
at least two actuators being mounted on the frame, controlled by the control unit corresponding to the lamps and the image acquisition units and being connected electronically to the mounting brackets to control the lamps and the image acquisition units to pivot relative to the substrate to required angles.

2. The substrate-check equipment as claimed in claim 1, wherein the conveyer is pervious to light.

3. The substrate-check equipment as claimed in claim 2, wherein each lamp further has a light emitted diode (LED) light being connected electronically to the adjusting unit.

4. The substrate-check equipment as claimed in claim 3, wherein the LED light is a LED tubular light.

5. The substrate-check equipment as claimed in claim 2, wherein each image acquisition unit is a camera with a linear charge coupled device (linear CCD).

6. The substrate-check equipment as claimed in claim 3, wherein each image acquisition unit is a camera with a linear CCD.

7. The substrate-check equipment as claimed in claim 4, wherein each image acquisition unit is a camera with a linear CCD.

8. The substrate-check equipment as claimed in claim 1, wherein the control unit is further connected electronically to the conveyer to control movement of the conveyer conveying the substrate.

* * * * *